United States Patent
Sasaki et al.

(10) Patent No.: US 9,066,676 B2
(45) Date of Patent: Jun. 30, 2015

(54) ENDOSCOPIC IMAGE DISPLAY APPARATUS

(75) Inventors: Wataru Sasaki, Tokyo (JP); Goro Miura, Tokyo (JP); Kunimasa Shimizu, Tokyo (JP); Atsushi Misawa, Tokyo (JP); Yasuhiro Asai, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 419 days.

(21) Appl. No.: 13/247,710

(22) Filed: Sep. 28, 2011

(65) Prior Publication Data

US 2012/0078046 A1    Mar. 29, 2012

(30) Foreign Application Priority Data

Sep. 28, 2010   (JP) ................. 2010-217961

(51) Int. Cl.

| A61B 1/04 | (2006.01) |
|---|---|
| A61B 1/06 | (2006.01) |
| A61B 6/00 | (2006.01) |
| A61B 1/00 | (2006.01) |
| A61B 1/05 | (2006.01) |

(52) U.S. Cl.
CPC ........... *A61B 1/0638* (2013.01); *A61B 1/00009* (2013.01); *A61B 1/00018* (2013.01); *A61B 1/00045* (2013.01); *A61B 1/05* (2013.01); *A61B 1/063* (2013.01); *A61B 1/0646* (2013.01); *A61B 1/0653* (2013.01)

(58) Field of Classification Search
CPC ........ A61B 1/05; A61B 1/042; A61B 1/0638; A61B 1/06; A61B 5/0071; G01J 3/10
USPC ......... 600/109, 101, 473, 476, 310, 468, 504, 600/178, 180, 317; 607/88, 89; 606/3; 348/65, 71, 223.1, 224.1, 655

See application file for complete search history.

(56) References Cited

U.S. PATENT DOCUMENTS

| 4,951,134 | A | * | 8/1990 | Nakasima et al. .............. 348/71 |
|---|---|---|---|---|
| 5,111,804 | A | * | 5/1992 | Funakoshi .................... 600/109 |
| 5,570,129 | A | * | 10/1996 | Hafele et al. ................ 348/223.1 |
| 5,749,830 | A | * | 5/1998 | Kaneko et al. ................ 600/160 |
| 5,827,190 | A | * | 10/1998 | Palcic et al. .................. 600/476 |
| 6,320,331 | B1 | * | 11/2001 | Iida et al. ...................... 315/293 |

(Continued)

FOREIGN PATENT DOCUMENTS

| JP | 63-155984 A | 6/1988 |
|---|---|---|
| JP | 05-328364 A | 12/1993 |

(Continued)

OTHER PUBLICATIONS

Japanese Application Official Action No. 2010-217961 issued on Oct. 29, 2013.

*Primary Examiner* — John P Leubecker
*Assistant Examiner* — Ronald D Colque
(74) *Attorney, Agent, or Firm* — Young & Thompson

(57) ABSTRACT

An endoscopic image display apparatus reads taken image data in which a taken image outputted from an endoscope is recorded, and reproduces and displays the taken image. The taken image data includes intensity information about a plurality of fundamental color components. The endoscopic image display apparatus includes an intensity changing unit which selectively reduces intensity of a specific color component in the taken image data by using the intensity information.

8 Claims, 13 Drawing Sheets

(56) References Cited

U.S. PATENT DOCUMENTS

| | | | | |
|---|---|---|---|---|
| 6,421,553 B1* | 7/2002 | Costa et al. | | 600/476 |
| 6,427,082 B1* | 7/2002 | Nordstrom et al. | | 600/476 |
| 6,471,636 B1* | 10/2002 | Sano et al. | | 600/109 |
| 6,496,719 B2* | 12/2002 | Hayashi | | 600/478 |
| 6,537,211 B1* | 3/2003 | Wang et al. | | 600/178 |
| 6,571,119 B2* | 5/2003 | Hayashi | | 600/477 |
| 6,574,502 B2* | 6/2003 | Hayashi | | 600/476 |
| 6,800,057 B2* | 10/2004 | Tsujita et al. | | 600/160 |
| 6,898,458 B2* | 5/2005 | Zeng et al. | | 600/476 |
| 7,008,374 B2* | 3/2006 | Hakamata | | 600/109 |
| 7,043,291 B2* | 5/2006 | Sendai | | 600/478 |
| 7,102,142 B2* | 9/2006 | Sendai | | 250/461.1 |
| 7,179,221 B2* | 2/2007 | Tsujita et al. | | 600/109 |
| 7,204,803 B2* | 4/2007 | Ueno et al. | | 600/109 |
| 7,221,388 B2 | 5/2007 | Sudo | | |
| 7,235,045 B2* | 6/2007 | Wang et al. | | 600/109 |
| 7,257,437 B2* | 8/2007 | Demos et al. | | 600/473 |
| 7,283,858 B2* | 10/2007 | Sendai | | 600/407 |
| 7,583,993 B2* | 9/2009 | Sendai | | 600/476 |
| 7,722,534 B2* | 5/2010 | Cline et al. | | 600/160 |
| 8,040,373 B2 | 10/2011 | Ayame | | |
| 8,167,794 B2* | 5/2012 | Matsumoto et al. | | 600/160 |
| 8,337,400 B2 | 12/2012 | Mizuyoshi | | |
| 8,451,328 B2* | 5/2013 | Yoshino et al. | | 348/65 |
| 8,581,972 B2 | 11/2013 | Iwasaki | | |
| 2001/0007920 A1* | 7/2001 | Hayashi | | 600/476 |
| 2001/0007921 A1* | 7/2001 | Hayashi | | 600/476 |
| 2001/0011708 A1* | 8/2001 | Hakamata | | 250/458.1 |
| 2001/0049473 A1* | 12/2001 | Hayashi | | 600/317 |
| 2002/0013512 A1* | 1/2002 | Sendai et al. | | 600/160 |
| 2002/0035330 A1* | 3/2002 | Cline et al. | | 600/476 |
| 2002/0103439 A1* | 8/2002 | Zeng et al. | | 600/476 |
| 2002/0105505 A1* | 8/2002 | Sendai | | 345/204 |
| 2002/0138008 A1* | 9/2002 | Tsujita et al. | | 600/473 |
| 2002/0165456 A1* | 11/2002 | Canpolat et al. | | 600/473 |
| 2002/0175993 A1* | 11/2002 | Ueno et al. | | 348/68 |
| 2002/0177751 A1* | 11/2002 | Ueno et al. | | 600/160 |
| 2002/0177780 A1* | 11/2002 | Sendai | | 600/476 |
| 2003/0001951 A1* | 1/2003 | Tsujita et al. | | 348/65 |
| 2003/0013937 A1* | 1/2003 | Tsujita et al. | | 600/109 |
| 2003/0135092 A1* | 7/2003 | Cline et al. | | 600/160 |
| 2003/0216626 A1* | 11/2003 | Tsujita et al. | | 600/321 |
| 2003/0218137 A1* | 11/2003 | Sendai | | 250/461.1 |
| 2004/0006275 A1* | 1/2004 | Demos et al. | | 600/476 |
| 2004/0006276 A1* | 1/2004 | Demos et al. | | 600/476 |
| 2004/0019253 A1* | 1/2004 | Tsujita et al. | | 600/118 |
| 2004/0037454 A1* | 2/2004 | Ozawa et al. | | 382/128 |
| 2004/0044275 A1* | 3/2004 | Hakamata | | 600/310 |
| 2004/0046865 A1* | 3/2004 | Ueno et al. | | 348/70 |
| 2004/0148141 A1* | 7/2004 | Tsujita et al. | | 702/190 |
| 2005/0027166 A1* | 2/2005 | Matsumoto et al. | | 600/162 |
| 2005/0065406 A1* | 3/2005 | Cline et al. | | 600/160 |
| 2005/0068427 A1 | 3/2005 | Sudo | | |
| 2005/0203423 A1* | 9/2005 | Zeng et al. | | 600/476 |
| 2005/0234302 A1* | 10/2005 | MacKinnon et al. | | 600/181 |
| 2005/0237416 A1* | 10/2005 | Hasegawa | | 348/335 |
| 2006/0058684 A1* | 3/2006 | Sendai | | 600/476 |
| 2006/0142640 A1* | 6/2006 | Takahashi | | 600/117 |
| 2006/0247537 A1* | 11/2006 | Matsumoto | | 600/478 |
| 2006/0252988 A1 | 11/2006 | Ayame | | |
| 2007/0015963 A1* | 1/2007 | Fengler et al. | | 600/109 |
| 2007/0112258 A1* | 5/2007 | Soyemi et al. | | 600/310 |
| 2007/0149858 A1* | 6/2007 | Ogawa et al. | | 600/181 |
| 2008/0004495 A1* | 1/2008 | Allen et al. | | 600/160 |
| 2008/0051664 A1* | 2/2008 | Demos et al. | | 600/473 |
| 2008/0074492 A1 | 3/2008 | Iwasaki | | |
| 2008/0177140 A1* | 7/2008 | Cline et al. | | 600/112 |
| 2008/0228037 A1* | 9/2008 | Cline et al. | | 600/160 |
| 2009/0012361 A1* | 1/2009 | MacKinnon et al. | | 600/118 |
| 2010/0039507 A1* | 2/2010 | Imade | | 348/68 |
| 2010/0168588 A1* | 7/2010 | Matsumoto et al. | | 600/478 |
| 2010/0198010 A1* | 8/2010 | Cline et al. | | 600/109 |
| 2010/0210904 A1* | 8/2010 | Cline et al. | | 600/109 |
| 2010/0280322 A1 | 11/2010 | Mizuyoshi | | |
| 2011/0074942 A1* | 3/2011 | Endo et al. | | 348/68 |
| 2012/0136209 A1* | 5/2012 | Kostenich et al. | | 600/109 |

FOREIGN PATENT DOCUMENTS

| | | |
|---|---|---|
| JP | 2000-221417 A | 8/2000 |
| JP | 2004-121549 A | 4/2004 |
| JP | 2006-068113 | 3/2006 |
| JP | 2006-255324 A | 9/2006 |
| JP | 2008-073345 A | 4/2008 |
| JP | 2009-297290 A | 12/2009 |

* cited by examiner

FIG. 11

| INSPECTION NO. | PATIENT ID | TIME ACCEPTED | INSPECTION KIND | REGION TO BE OBSERVED |
|---|---|---|---|---|
| 031 | ID00003 | 9:30 | UPPER ENDOSCOPIC INSPECTION | ESOPHAGUS, GASTER |
| 032 | ID00009 | 9:40 | UPPER ENDOSCOPIC INSPECTION | GASTER, DUODENUM |
| 033 | ID00015 | 10:10 | LOWER ENDOSCOPIC INSPECTION | LARGE INTESTINE |
| ⋮ | ⋮ | ⋮ | ⋮ | ⋮ |

ENDOSCOPIC IMAGE DISPLAY APPARATUS

CROSS-REFERENCE TO RELATED APPLICATIONS

This application claims the benefit of Japanese Patent Application No. 2010-217961, filed on Sep. 28, 2010, the entire contents of which are hereby incorporated by reference, the same as if set forth at length; the entire of which are incorporated herein by reference.

BACKGROUND OF THE INVENTION

1. Technical Field

The present invention relates to an endoscopic image display apparatus which reads taken image data in which a taken image outputted from an endoscope has been recorded, and displays the taken image.

2. Description of Related Art

Endoscopes which can take an image by irradiating the inside of a to-be-inspected body with white illumination light to thereby obtain an observed image are widely used. In addition to normal imaging with visible light, some endoscopes can perform narrow-band imaging in which short-wavelength visible narrow-band light (special light) is radiated so that capillary blood vessels in a body tissue surface layer or microscopic patterns in a mucosal surface can be highlighted and displayed (for example, see JP-2006-068113-A).

Generally, short-wavelength visible light (for example, violet or blue light) is shallow in invasion depth into body tissue, while long-wavelength visible light (for example, red light) is deep in invasion depth into body tissue. In normal imaging using white illumination light containing long-wavelength light, an image including light reflected from a comparatively deep region of body tissue is observed. On the other hand, since short-wavelength light is used in special light imaging, an image of light reflected from a surface layer of the tissue is chiefly observed. Accordingly, the images observed by these two types of imaging differ from each other in spite of the same observed position. In use, those images are suitably switched from one to the other during endoscopic diagnosis.

SUMMARY

Plenty of B light components such as violet or blue light components are contained in illumination light for narrow-band imaging. For this reason, an image taken with illumination light in narrow-band imaging differs in tinge of color from an image obtained with white illumination light in normal imaging. As a result, when an image obtained in narrow-band imaging is subjected to image processing in accordance with any kind of image processing algorism that is prepared in advance for images obtained in normal imaging, luminance value failure etc. of the image occurs so that the image cannot be an intended image. Description in JP-2006-068113-A is made that different white balance correction processings are carried out in accordance with normal light and narrow-band light respectively. However, an image taken in narrow-band imaging has a different tinge of color from an image taken in normal imaging due to the difference in spectra of illumination light. Thus, it is difficult to remove the difference in tinge of color completely by white balance.

There are some endoscopic systems in which a motion picture outputted from an endoscope is recorded on a recording device and secondarily read after inspection. However, only one of an image obtained in narrow-band imaging and an image obtained in normal imaging is generally recorded as the motion picture recorded on the recording device. Therefore, even if it is desired that the color tone of the image obtained in the narrow-band imaging is changed to color tone of an image obtained with white light in the normal imaging to thereby make comparison between the two images feasible, it is practically difficult to perform this. Thus, the real situation is that there are many restrictions in the range of use of the image obtained in the narrow-band imaging even when the image is recorded.

An object of the invention is to provide an endoscopic image display apparatus in which even a recorded image obtained using special light in narrow-band imaging or the like can be easily converted into an image having color tone in normal imaging and displayed so as to make comparison between the images or application of various image processings thereto feasible, so that accuracy in endoscopic diagnosis can be improved.

The invention is constituted as below.

An endoscopic image display apparatus reads taken image data in which a taken image outputted from an endoscope is recorded, and reproduces and displays the taken image. The taken image data includes intensity information about a plurality of fundamental color components. The endoscopic image display apparatus includes an intensity changing unit which selectively reduces intensity of a specific color component in the taken image data by using the intensity information.

According to the invention, even a recorded image obtained using special light in narrow-band imaging or the like can be easily converted into an image having color tone in normal imaging and displayed so as to make comparison between the images or application of various image processings thereto feasible, so that accuracy in endoscopic diagnosis can be improved.

BRIEF DESCRIPTION OF THE DRAWINGS

FIG. 11 is an explanatory view showing inspection orders and their contents recorded in an inspection order database.

DETAILED DESCRIPTION OF EMBODIMENTS OF THE INVENTION

An exemplary embodiment of the invention will be described below in detail with reference to the drawings.

Figure 1:
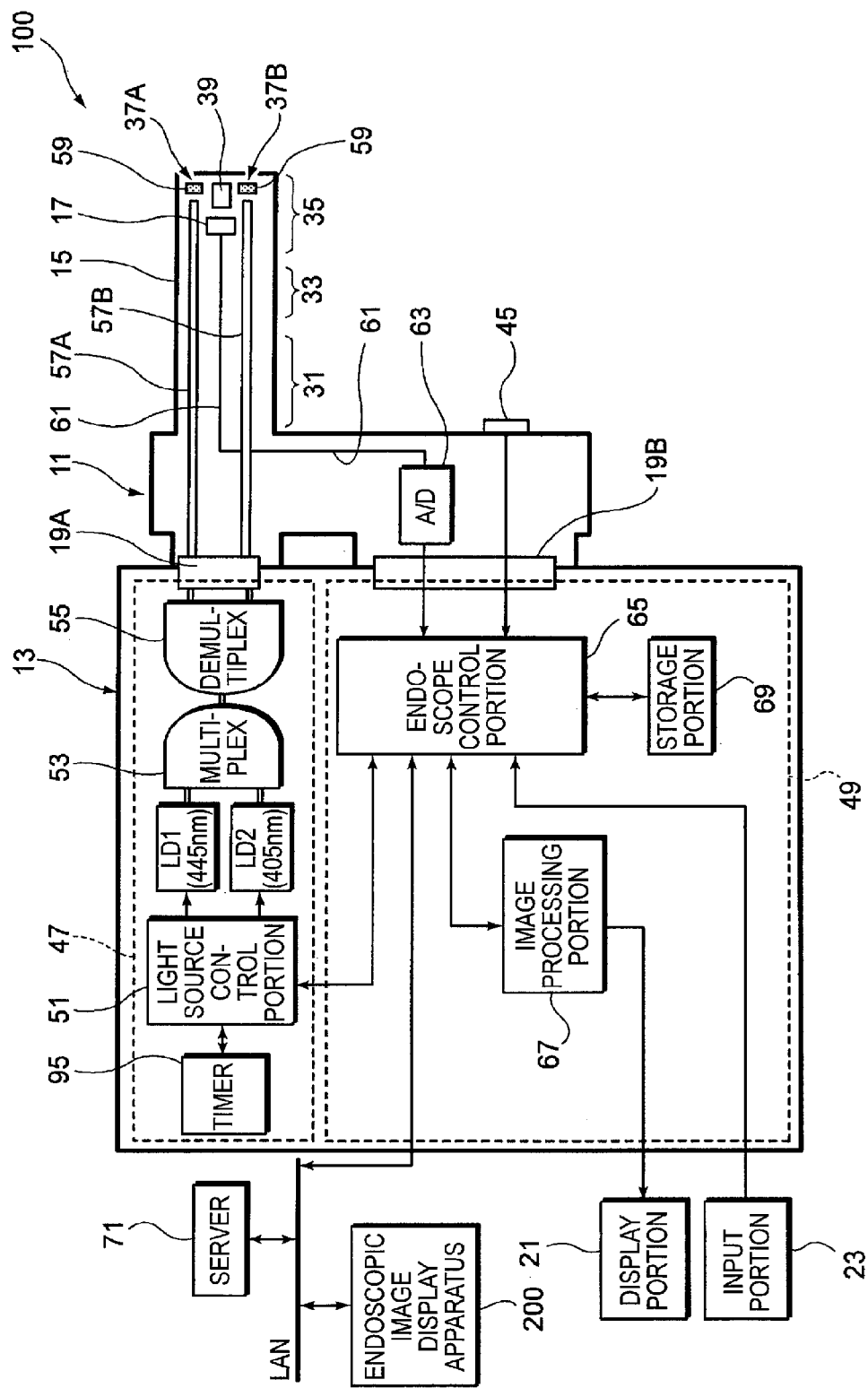
FIG. 1 is a block configuration diagram of an endoscopic apparatus for explaining an exemplary embodiment of the invention.
Figure 2:
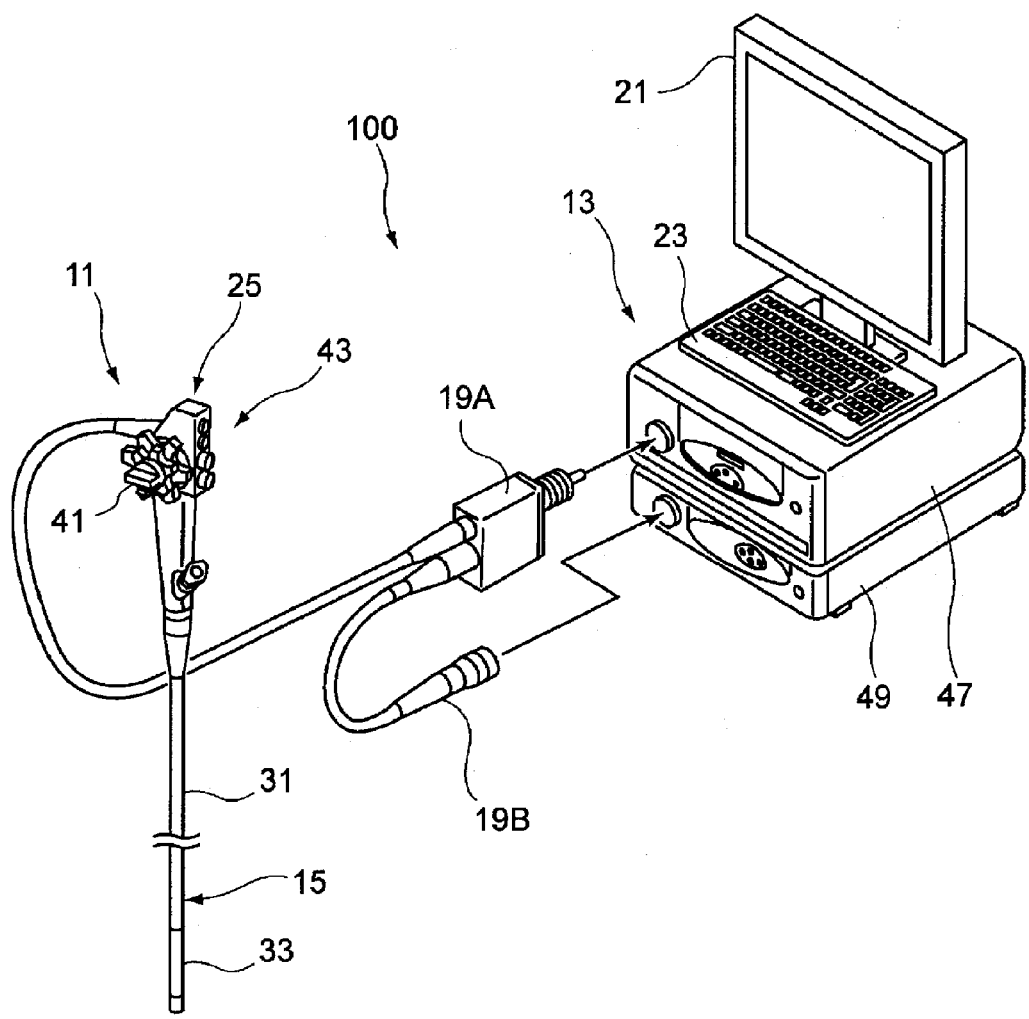
FIG. 2 is an external view as an example of the endoscopic apparatus shown in FIG. 1.

FIG. 1 is a conceptual block configuration diagram of an endoscopic apparatus for explaining the exemplary embodiment of the invention. FIG. 2 is an external view as an example of the endoscopic apparatus shown in FIG. 1.

As shown in FIGS. 1 and 2, an endoscopic apparatus 100 has an endoscope 11, and an endoscope control device 13 to which the endoscope 11 is connected. The endoscope 11 is an electronic endoscope which has an illumination optics for emitting illumination light from a front end of an endoscope insertion portion 15, and an image-taking optics including an image-taking element 17 for taking an image of a to-be-observed region. The endoscope 11 is removably connected to the endoscope control device 13 through connector portions 19A and 19B. A display portion 21 and an input portion 23 are connected to the endoscope control device 13. The display portion 21 displays image information or the like transmitted from the endoscope 11. The input portion 23 accepts input operation.

As shown in FIG. 2, the endoscope 11 has the endoscope insertion portion 15, an operation portion 25, and the connector portions 19A and 19B. The endoscope insertion portion 15 is inserted into a to-be-inspected body. The operation portion 25 performs operation for bending the front end of the endoscope insertion portion 15 or operation for observation. The connector portions 19A and 19B are connected to the operation portion 25 through a universal cord 27. Though not shown, various channels such as a forceps channel for inserting a treatment tool for sampling a tissue, a channel for feeding air/water, etc. are provided internally in the endoscope insertion portion 15.

The endoscope insertion portion 15 is constituted by a soft portion 31 with flexibility, a bendable portion 33, and an endoscope front end portion (hereinafter also referred to as front end portion) 35. As shown in FIG. 1, irradiation ports 37A and 37B for irradiating a to-be-observed region with light, and the image-taking element 17 such as a CCD (Charge Coupled Device) image sensor or a CMOS (Complementary Metal-Oxide Semiconductor) image sensor for acquiring image information of the to-be-served region are disposed in the endoscope front end portion 35. In addition, an objective lens unit 39 is attached to the front side of an optical path of the image-taking element 17.

The bendable portion 33 is provided between the soft portion 31 and the front end portion 35 so that the bendable portion 33 can be bent by the rotating operation of an angle knob 41 disposed in the operation portion 25. The bendable portion 33 can be bent in any direction and at any angle so as to set the direction of light emitted from the irradiation ports 37A and 37B of the endoscope front end portion 35 and the observing direction of the image-taking element 17 toward a desired to-be-observed region. Though not shown, a cover glass or a lens is also disposed on the outer side of each irradiation port 37A, 37B of the endoscope insertion portion 15.

In addition to the angle knob 41, switches 43 with various functions are disposed in the operation portion 25. An observation mode changeover switch 45 shown in FIG. 1 is also disposed.

The endoscope control device 13 is provided with a light source device 47 and a processor 49, and connected to the endoscope 11 through the connector portions 19A and 19B. The light source device 47 generates illumination light to be supplied to the irradiation ports 37A and 37B of the endoscope front end portion 35. The processor 49 applies image processing to an image signal from the image-taking element 17. In addition, the aforementioned display portion 21 and the aforementioned input portion 23 are connected to the processor 49. The processor 49 applies image processing to an image-taking signal transmitted from the endoscope 11, based on an instruction from the operation portion 25 of the endoscope 11 or from the input portion 23, so as to generate and supply image data to the display portion 21.

The light source device 47 is provided with a blue laser light source LD1 and a violet laser light source LD2 as light emitting sources. The blue laser light source LD1 is a semiconductor light emitting element with a central wavelength of 445 nm. The violet laser light source LD2 is a semiconductor light emitting element with a central wavelength of 405 nm. Emissions of the light sources LD1 and LD2 are controlled individually by a light source control portion 51 so that the light quantity ratio between the light emitted from the blue laser light source LD1 and the light emitted from the violet laser light source LD2 can be changed desirably. That is, the light source control portion 51 can control the color tone of the illumination light desirably.

As the blue laser light source LD1 and the violet laser light source LD2, broad-area type InGaN-based laser diodes may be used. In addition, InGaNAs-based laser diodes or GaNAs-based laser diodes may be also used. Further, a configuration using light emitters such as light emitting diodes may be used as the aforementioned light sources.

Laser lights emitted from the light sources LD1 and LD2 are inputted to optical fibers through condenser lenses (not shown) respectively, and guided to the connector portion 19A through a combiner 53 as a multiplexer and a coupler 55 as a demultiplexer.

Laser light in which the blue laser light with a central wavelength of 445 nm and the violet laser light with a central wavelength of 405 nm are multiplexed is supplied to the connector portion 19A, and guided to the endoscope front end portion 35 through optical fibers 57A and 57B respectively. The blue laser light excites a fluorescent substance 59 as a wavelength conversion member disposed in the light outgoing terminal of each optical fiber 57A, 57B of the endoscope front end portion 35 so as to generate fluorescence. In addition, a part of the blue laser light is transmitted through the fluorescent substance 59 as it is, and emitted as white illumination light together with the aforementioned fluorescence. On the other hand, the violet laser light is transmitted without intensively exciting the fluorescent substance 59, and emitted as illumination light with a narrow-band wavelength.

Figure 3:
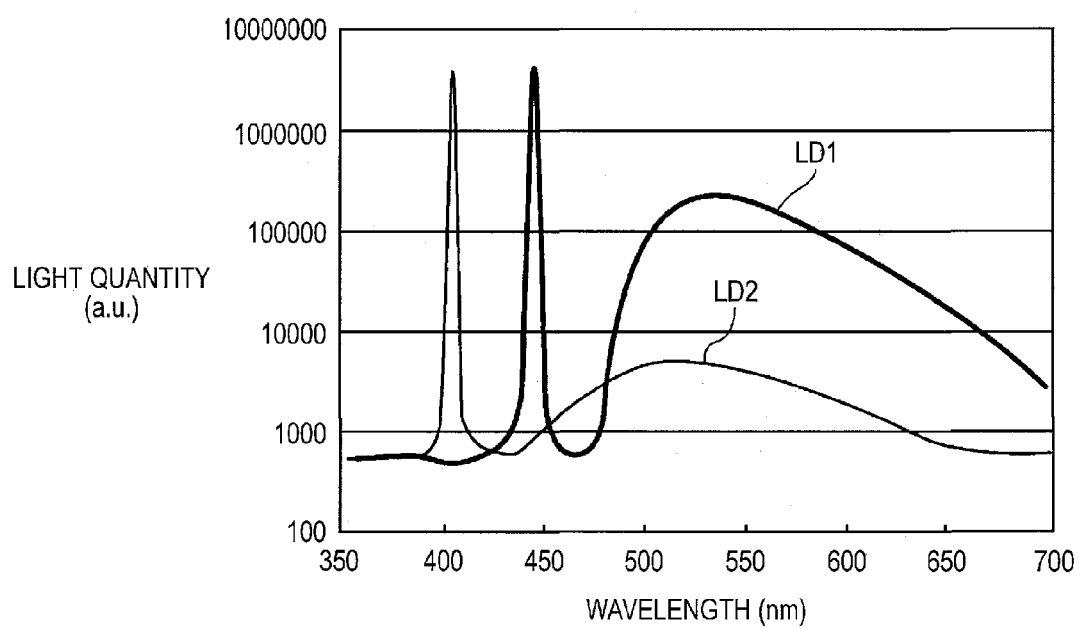
FIG. 3 is a graph showing spectroscopic profiles of illumination lights emitted from irradiation ports as violet laser light from a violet laser light source and blue laser light from a blue laser light source respectively.

FIG. 3 shows spectroscopic profiles of illumination lights emitted from the irradiation ports 37A and 37B by the violet laser light from the violet laser light source LD2 and the blue laser light from the blue laser light source LD1 respectively. In FIG. 3, the violet laser light is expressed by an emission line with a central wavelength of 405 nm, and the blue laser light is expressed by an emission line with a central wavelength of 445 nm. In addition, light emitted by the fluorescent substance 59 excited by the blue laser light has a spectral intensity distribution in which emission intensity increases in a wavelength band of from about 450 nm to about 700 nm. White illumination light is formed by the profile of the excited emitted light and the blue laser light.

The white light mentioned herein is not strictly limited to light containing all the wavelength components of visible light, but may be any light if it contains light of a special wavelength band such as R, G or B. For example, light containing a wavelength component between green and red, light containing a wavelength component between blue and green, or the like, may be broadly included in the white light.

The fluorescent substance 59 is arranged to include a plurality of kinds of fluorescent substances (such as a YAG-based fluorescent substance, a fluorescent substance containing BAM (BaMgAl$_{10}$O$_{17}$) or the like, etc.) which absorb a part of the blue laser light so as to be excited to emit light between green and yellow. As a result, the excited light of green to yellow using the blue laser light as excitation light is combined with the blue laser light which is not absorbed but transmitted through the fluorescent substance 59. Thus, white (pseudo white) illumination light is formed.

Return to FIG. 1 again, and description will be made with reference thereto. As described above, the illumination light in which the blue laser light and the excited emitted light from the fluorescent substance 59 (white illumination light), and the illumination light (narrow-band light) formed by the violet laser light are set in a desired light quantity ratio by the light source control portion 51 is radiated from the endoscope front end portion 35 toward a to-be-observed region of a to-be-inspected body. The condition of the to-be-observed region irradiated with the illumination light is focused and imaged on the image-taking element 17 by the objective lens unit 39. That is, taken image data obtained thus is data of an image taken by use of illumination light with a spectroscopic profile including laser light and light emitted from a fluorescent substance excited by the laser light.

After the image-taking, an image signal of the taken image is outputted from the image-taking element 17, passed through a scope cable 61, and transmitted to an A/D converter 63 in which the image signal is converted into a digital image signal and inputted to an endoscope control portion 65 of the processor 49 through the connector portion 19b. The endoscope control portion 65 sends the inputted digital image signal to an image processing portion 67. The image processing portion 67 converts the digital image signal into image data and performs suitable image processing on the image data to generate endoscopic image data. Then, the endoscope control portion 65 outputs the obtained endoscopic image data as an endoscopically observed image to the display portion 21 so as to display the endoscopically observed image on the display portion 21. The endoscope control portion 65 controls a storage portion 69 consisting of a memory or a storage device to store endoscopically observed image, if necessary.

The storage portion 69 may be built in the processor 49 as in the illustrated example. Alternatively the storage portion 69 may be connected to the processor 49 through a network or built in a server 71 connected through a network.

Figure 4:
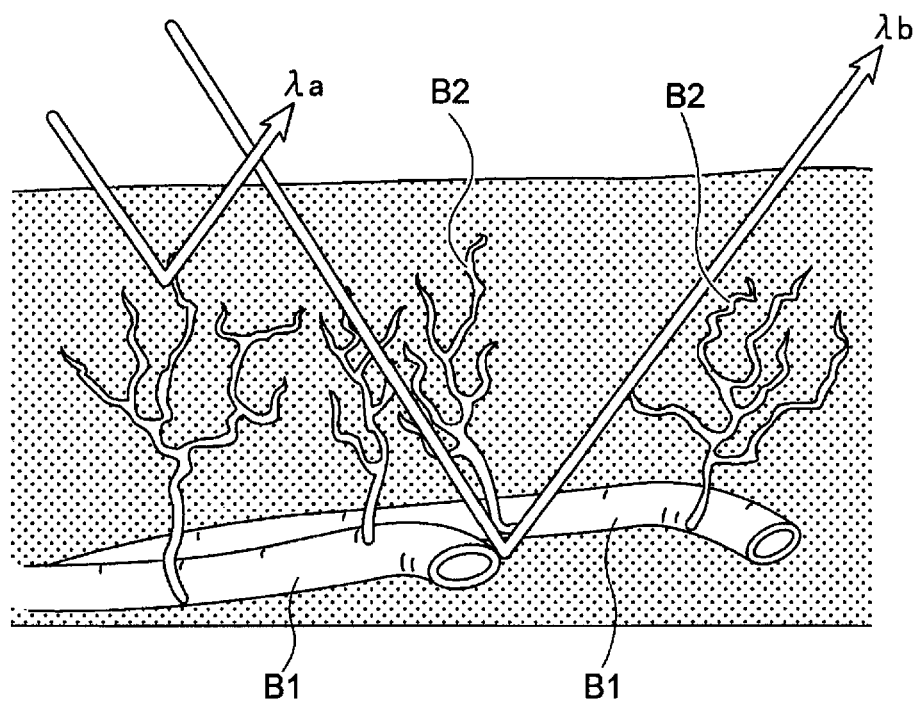
FIG. 4 is an explanatory view schematically showing blood vessels in a mucosal surface layer of a body tissue.

FIG. 4 shows an explanatory view schematically depicting blood vessels in a mucosal surface layer of a body tissue. As for the mucosal surface layer of the body tissue, it has been reported that capillary blood vessels B2 such as branching vessel networks are formed between each blood vessel B1 in a mucosal deep layer and the mucosal surface layer, and a lesion of the body tissue appears in the microstructure including the capillary blood vessels B2 or the like. Thus, in endoscopic diagnosis, the capillary blood vessels of the mucosal surface layer are highlighted and observed in an image to detect a microscopic lesion in an early stage or diagnose the range of the lesion.

When illumination light is incident on a body tissue, the incident light is propagated diffusely in the body tissue. The scattering characteristic of the body tissue has a tendency to increase in a shorter wavelength due to the wavelength dependency of the absorption/scattering characteristic of the body tissue. That is, the invasion depth of the illumination light changes in accordance with the wavelength of the light. Accordingly, blood vessel information from capillary blood vessels in a mucosal surface layer can be obtained in a wavelength band λa where the illumination light has a wavelength near 400 nm, and blood vessel information also including blood vessels in a deep layer can be obtained in a wavelength band λb where the illumination light has a wavelength near 500 nm. Therefore, a light source with a central wavelength of 360 to 800 nm, preferably 365 to 515 nm, is used for observation of blood vessels in a body tissue. Particularly for observation of blood vessels in a surface layer, a light source with a central wavelength of 360 to 470 nm, preferably 400 to 420 nm, is used. In addition, microscopic patterns in the mucosal surface of the body tissue can be also highlighted and displayed in the aforementioned wavelength range in the same manner as the capillary blood vessels.

Figure 5A:
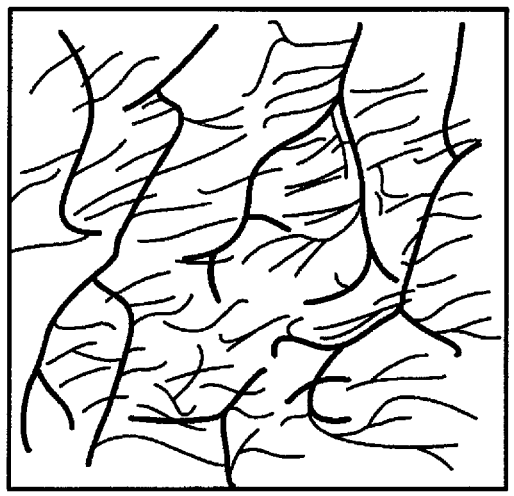
FIG. 5A is an explanatory view schematically showing an image observed by the endoscopic apparatus using narrow-band light containing plenty of short-wavelength visible light components as illumination light by way of example.
Figure 5B:
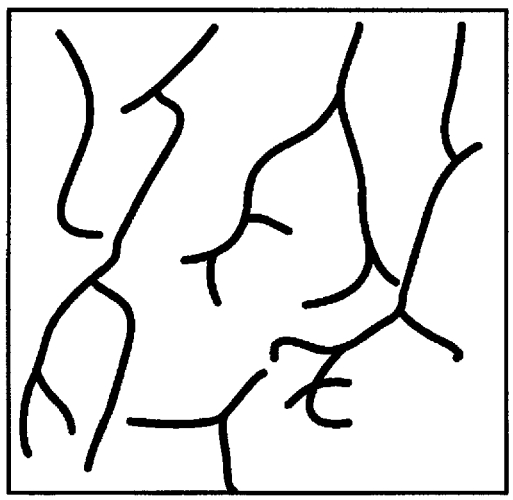
FIG. 5B is an explanatory view showing an observed image using white light as illumination light.

FIGS. 5A and 5B show a schematic example of display of an image observed by an endoscopic apparatus. When narrow-band light containing plenty of short-wavelength visible components is used as illumination light, an image in which microscopic capillary blood vessels in a mucosal surface layer or microscopic patterns in the mucosal surface layer are reflected clearly is obtained (FIG. 5A). When white light is used as illumination light, a general image of an affected area in which blood vessels in a mucosal deep layer are comparatively reflected is obtained (FIG. 5B).

That is, in an observed image obtained by concurrent irradiation with the white illumination light and the narrow-band light, the microscopic capillary blood vessels in the mucosal surface layer of the body tissue or the microscopic patterns in the mucosal surface layer can be highlighted to make it easy to identify the characteristics of the affected area or the observed position. That is, an observed image in which the affected area can be endoscopically diagnosed easily can be obtained. In the endoscopic apparatus 100 configured as shown in FIG. 1, therefore, the emission quantities of the white light (blue laser light and light emitted by the fluorescent substance) and the narrow-band light (violet laser light) emitted from the endoscope front end portion 35 can be changed continuously and independently of each other by the light source control portion 51 so that reflected lights of the two illumination lights can be included in one frame of a taken image.

The emission quantity ratio between the white illumination light and the narrow-band light is set as a suitable ratio. For example, the emission quantity ratio between the white illumination light: the narrow-band light is 1:4 to 1:8. Thus, it is possible to acquire an observed image in which an observed region can be clearly reflected by white illumination light while blood vessels in a mucosal surface layer or microscopic patterns in the mucosal surface can be highlighted by the narrow-band light so as to make it easy to observe a microscopic structure of the blood vessels or pits belonging thereto.

Next, description will be made in the case where data of an endoscopic image taken by the endoscopic apparatus 100 configured thus is stored in the storage portion and image information obtained by performing arithmetic operation on the stored endoscopic image data is displayed.

Figure 6:
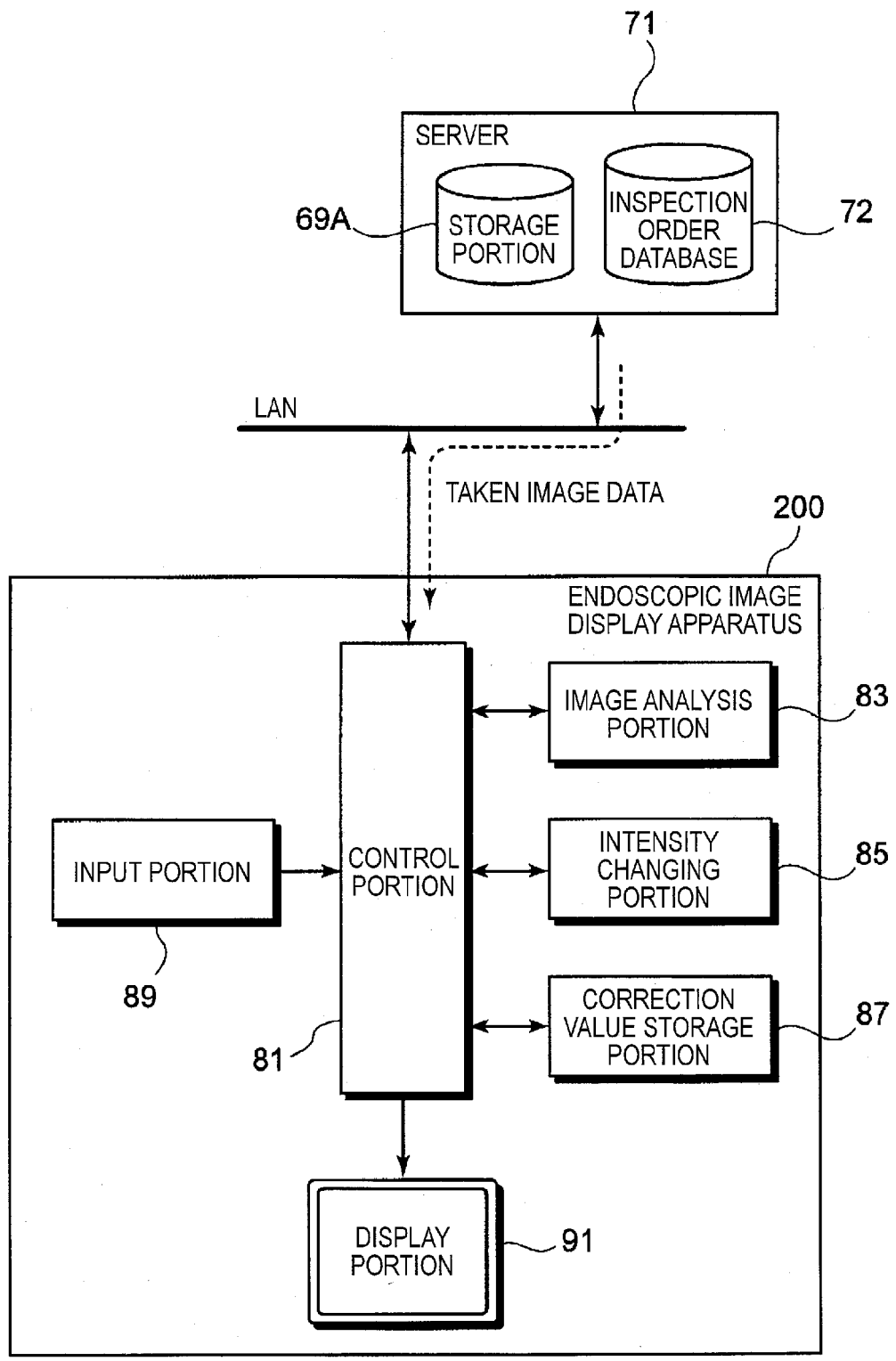
FIG. 6 is a block diagram of an endoscopic image display apparatus.

FIG. 6 is a block diagram of an endoscopic image display apparatus. An endoscopic image display apparatus 200 is connected to the network to which the endoscopic apparatus 100 is connected. The endoscopic image display apparatus 200 is an apparatus which reads taken image data in which a taken image outputted from the endoscope 11 has been recorded, and which reproduces and displays the taken image as it is or after suitable arithmetic operation is performed on the taken image.

The endoscopic image display apparatus 200 has an intensity changing unit for selectively reducing the intensity of a specific color component of the taken image data. The endoscopic image display apparatus 200 can not only reproduce and display the taken image data just as recorded but also change the color tone of an image in narrow-band imaging using the aforementioned narrow-band light into the color tone of an image in white light imaging and display the image with the changed color tone.

The endoscopic image display apparatus 200 has a control portion 81, an image analysis portion 83, an intensity changing portion 85 and a correction value storage portion 87. The image analysis portion 83 analyzes data of a taken image. The intensity changing portion 85 changes the intensity of a specific color component of the taken image based on a result of the analysis. The correction value storage portion 87 stores a correction value for increasing/decreasing a correction coefficient with which the intensity changing portion 85 can change the intensity of the specific color component. In addition, the endoscopic image display apparatus 200 is arranged to include an input portion 89 for inputting various instructions to the control portion 81, and a display portion 91 for displaying an image whose intensity has been changed.

Assume now that data of a taken image obtained under illumination light containing narrow-band light by the endoscopic apparatus 100 has been stored in a storage portion 69A of a server 71 connected to the endoscopic apparatus 100 through a network. Here, description will be made below on processing of the endoscopic image display apparatus 200 for reading taken image data from the storage portion 69A, performing desired image processing on the taken image data and displaying the processed image data on the display portion 91.

The endoscopic image display apparatus 200 selectively reads data of a desired taken image from a data group of a plurality of taken images in the storage portion 69A. The taken image data is still picture or motion picture data having a plurality of fundamental color components including blue (B), green (G) and red (R). The taken image data is image information defined by intensity values (luminance values) of B, G and R in each pixel. When the taken image data is data recorded in narrow-band imaging, the B value of the taken image data generally has a higher intensity level than any other value of the R and G values.

Figure 7:
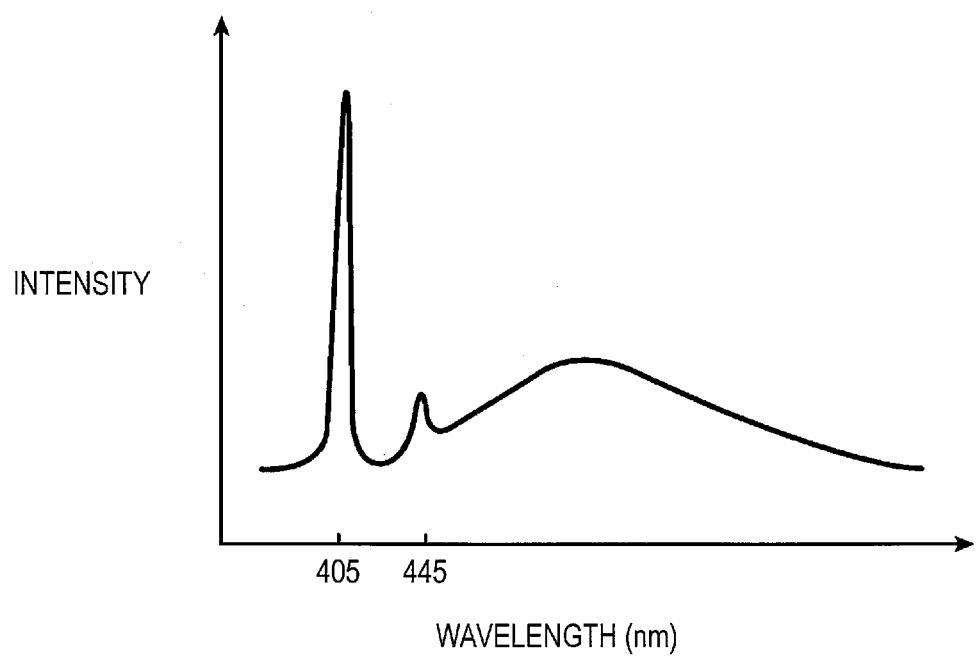
FIG. 7 is a graph showing a spectroscopic profile of illumination light in narrow-band imaging.

That is, in the narrow-band imaging, taken image data is produced by irradiation with illumination light having a distribution profile as shown in FIG. 7. Thus, the taken image data has higher intensity in the component of the narrow-band light (especially violet light with a central wavelength of 405 nm) than the component of any other wavelength band light. Thus, the image taken in the narrow-band imaging is an image tinged with blue.

When such a taken image tinged with blue is subjected to image processing in accordance with various image processing algorithms prepared in advance for images obtained in normal imaging, that is, white illumination light imaging, luminance value failure etc. of the image occurs so that the image cannot be an intended image. In addition, it may be desired that the taken image tinged with blue in the narrow-band imaging is viewed with color tone in the normal imaging. To this end, the endoscopic image display apparatus 200 configured thus has a function of selectively reducing the intensity of a specific color component corresponding to illumination light with comparatively high intensity even in data of an image taken in the narrow-band imaging, so as to artificially change the color tone of the image into color tone of an image obtained by white light illumination. Thus, the data of the image taken in the narrow-band imaging is converted to have color tone in the normal imaging so that the image taken in the narrow-band imaging can be observed in contrast with an image taken in the normal imaging in the same position. In addition, image processing in accordance with various image processing algorithms can be performed normally.

Figure 8:
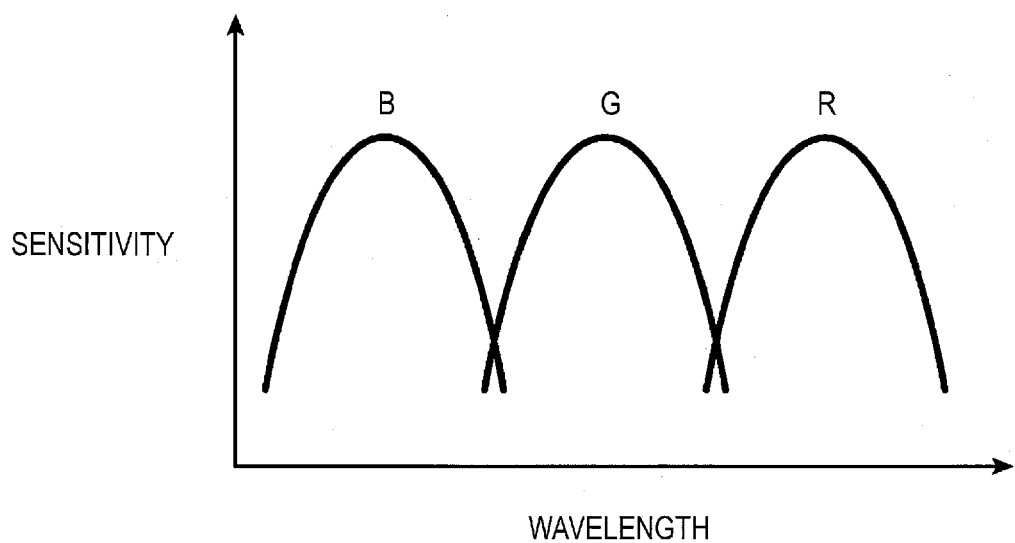
FIG. 8 is a graph showing the spectral sensitivity characteristic of an image-taking element.

Specifically, a B light component detected by the image-taking element 17 whose spectral sensitivity characteristic is shown in FIG. 8 has a higher intensity level than any of G and R light components in illumination light having a spectroscopic profile shown in FIG. 7 for narrow-band imaging. Therefore, data of an image taken in the narrow-band imaging by the image-taking element is arithmetically processed in the following manner to change the color tone of the image.

Assume that $Fbp_{ij}$ designates the B color component of the taken image data; $Fgp_{ij}$, the G color component of the same; $Frp_{ij}$, the R color component of the same; $Fbq_{ij}$, the B color component of the taken image data whose color tone has been changed; $Fgq_{ij}$, the G color component of the same; $Frq_{ij}$, and the R color component of the same. In this case, the taken image data ($Fbp_{ij}$, $Fgp_{ij}$, $Frp_{ij}$) whose color tone has been changed are obtained from Expressions (1) to (3) using correction coefficients K. The indexes i and j express a pixel position of the taken image.

$$Fbq_{ij}=Kb \cdot Fbp_{ij} \tag{1}$$

$$Fgq_{ij}=Kg \cdot Fgp_{ij} \tag{2}$$

$$Frq_{ij}=Kr \cdot Frp_{ij} \tag{3}$$

Figure 9:
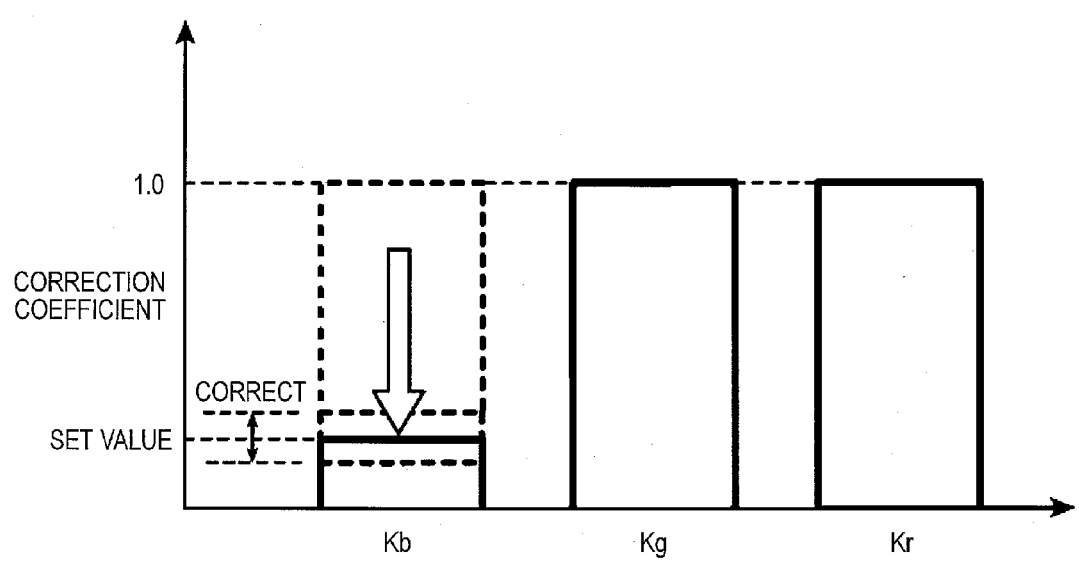
FIG. 9 is an explanatory view showing correction coefficients for B, G and R.

In the aforementioned Expressions, the correction coefficients Kb, Kg and Kr are set to selectively reduce the intensity value of the B color component of the taken image data (Fbp, Fgp, Frp) whose color tone has been changed. For example, an intended value for reducing the intensity of the B color component is set correspondingly to at least one of the G and R color components other than the B color component. In the aforementioned example, in accordance with the emission quantity ratio between the white illumination light and the narrow-band light, the correction coefficient Kb is set in a range of from ¼ to ⅛ and the correction coefficients Kg and Kr are set at 1, as shown in FIG. 9.

Figure 10:
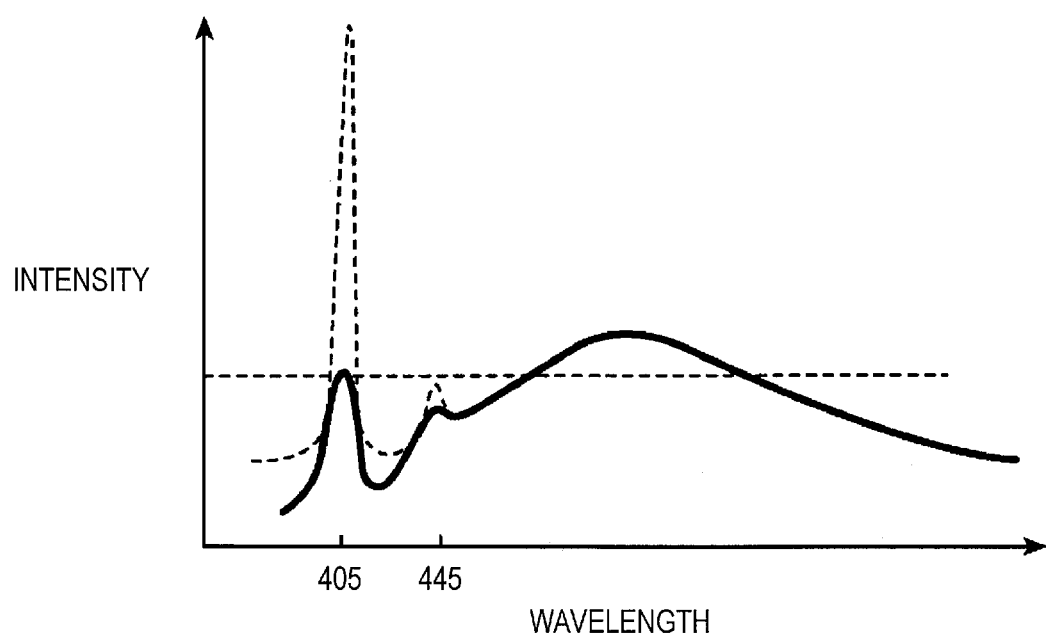
FIG. 10 is a graph showing a spectroscopic profile of illumination light for an image equivalent to taken image data whose intensity has been changed.

The image whose color tone has been changed by the correction coefficient Kb is artificially equivalent to an image taken by illumination light with a spectroscopic profile as shown in FIG. 10. That is, the taken image data after the change becomes an image close to an image taken by irradiation with illumination light in which the intensity of the narrow-band light component near the central wavelength of 405 nm shown in FIG. 7 has been selectively reduced so that the illumination light has a flat spectroscopic profile close to that of white light. In other words, the value of the correction coefficient Kb is set at a value by which data of an image taken in narrow-band imaging and highlighted with the B light component can be converted into data of an image taken in white illumination light imaging.

The aforementioned processing will be described with reference to FIG. 6. When there is a request for intensity changing processing from the input portion 89 in the endoscopic image display apparatus 200 shown in FIG. 6, the image analysis portion 83 analyzes differences in intensity among the B color component, the G color component and the R color component in the taken image data read from the storage portion 69A of the server 71, and decides, out of the fundamental colors of the taken image data, a specific color component whose intensity should be reduced. In an image taken in the narrow-band imaging, the blue color component is the specific color component.

The intensity changing portion 85 changes the intensity of the specific color component decided by the image analysis portion 83, based on the aforementioned Expressions (1) to (3). The intensity changing portion 85 generates a taken image signal in which the intensity of the specific color component has been changed. The control portion 81 converts the taken image signal into a display signal and displays the display signal on the display portion 91.

The correction coefficients Kb, Kg and Kr may not be set as predetermined default values but may be changed desirably by operation of the input portion 89. For example, the input portion 89 is constituted by a rotary switch, a slide switch or the like so that each correction coefficient can be changed stepwise by operation of the switch. Alternatively, a volume switch or the like may be used so that each correction coefficient can be adjusted to increase/decrease continuously to an arbitrary value. When the correction coefficients are set by the input portion 89, the input portion 89 can be operated while an image displayed on the display portion 91 is observed. Thus, the correction coefficients can be adjusted while the degree of change in the intensity of the specific color component is visually confirmed. In this manner, the image can be adjusted into a desired image easily.

Since the intensity of the specific color component can be changed arbitrarily, the condition of microscopic blood vessels different in depth direction from a tissue surface layer can be confirmed on an image when the intensity of the blue color component in the aforementioned data of the image taken in the narrow-band imaging is changed. Thus, the 3D distribution of blood vessels in the body tissue of the patient can be looked into so that the accuracy of diagnosis is improved.

When taken image data is data of an image taken with illumination light having a broad spectroscopic profile including narrow-band light based on laser light and light emitted from a fluorescent substance excited by the laser light, it is easy to adjust only the intensity level of the narrow-band light component based on the laser light. For example, when taken image data is obtained by an image-taking element which detects a plurality of fundamental color components, the narrow-band light can be set not to be detected across a plurality of the fundamental color components but to belong to only one fundamental color component (for example, blue) different from the light emitted from the excited fluorescent substance. Thus, only the intensity of the fundamental color component the narrow-band light belongs to can be corrected easily.

In addition, the correction value storage portion 87 stores table information for deciding the correction coefficients Kb, Kg and Kr. The values of the correction coefficients Kb, Kg and Kr decided by an operator of the endoscopic image display apparatus 200 may be corrected using the table information so as to increase/decrease in accordance with the endoscope or image-taking conditions. Thus, the intensity can be changed more accurately.

For example, the values of the correction coefficients Kb, Kg and Kr are corrected to increase/decrease in the following cases:

1) the correction coefficients are corrected to increase/decrease in accordance with a to-be-observed region of a to-be-inspected body reflected in taken image data.
2) the correction coefficients are controlled to increase/decrease in accordance with a calibration result of the image-taking optics of the endoscopic apparatus 100.
3) the correction coefficients are controlled to increase/decrease in accordance with the total lighting time of each light source LD1, LD2 of the light source device 47.

Information about the to-be-observed region of the to-be-inspected body, information about the calibration result and information about the total lighting time are recorded in a header portion of a data recording structure of taken image data when the taken image data is recorded into the storage portion 69A.

As for the to-be-observed region of the to-be-inspected body, when data of an image taken by the endoscopic apparatus is recorded into the storage portion 69A shown in FIG. 6, the endoscopic apparatus refers to an inspection order database 72 of the server 71 to determine an inspection the taken image data to be recorded is for. Information about the to-be-observed region corresponding to the image is written into a header portion of the taken image data.

As shown in inspection orders and their contents recorded in the inspection order database in FIG. 11, taken image data of an inspection performed by the endoscopic apparatus is associated with an inspection No., a patient ID, etc., so that the inspection order the taken image data belongs to can be identified. With reference to the contents of the identified inspection order, the endoscopic apparatus writes information about a to-be-observed region of the inspection order, such as "esophagus", "gaster" or "duodenum", into the header portion of the taken image data on the way of the endoscopic inspection or after the inspection.

In the endoscopic image display apparatus 200 which has read the taken image data, the control portion 81 reads information about the to-be-observed region from the header portion of the taken image data. The control portion 81 obtains correction values corresponding to the to-be-observed region with reference to the correction value storage portion 87. Since the tinge of an image varies in accordance with the to-be-observed region of a patient, correction values are registered in advance in the correction value storage portion 87 as follows. That is, correction values with which the intensity of the R color component will be reduced are registered for "gaster" whose image will be tinged with red, and correction values with which the intensities of the G color component and the R color component will be reduced are registered for "duodenum" whose image will be tinged with yellow. That is, suitable correction values are obtained from the correction value storage portion 87 in accordance with the to-be-observed region of the taken image data, and an intended value of intensity to be reduced for the specific color component of the taken image data is corrected based on the correction values. That is, the values of the correction coefficients Kb, Kg and Kr once set by the identified specific color component are corrected to increase/decrease based on the correction values in accordance with the to-be-observed region.

Next, description will be made in the case where the correction coefficients are corrected to increase/decrease in accordance with the calibration result of the image-taking optics. For white balance adjustment, a cylindrical white cap whose inside is whitened is attached to the front end of the endoscope insertion portion 15 (see FIG. 2) before endoscopic inspection, and an image is taken by irradiation with predetermined illumination light. The balance among intensity values of the B color component, the G color component and the R color component is adjusted so that the color tone of the image taken in that condition can be displayed in proper white.

The storage portion 69 (see FIG. 1) stores information about the set white balance. With reference to the information about the white balance, the image processing portion 67 corrects an image signal supplied from the image-taking element 17 to always have proper color balance.

However, when the intensity of the specific color component is selectively reduced, it is not necessary to adjust the white balance of the taken image data. It is rather preferable to recover the intensity value where the white balance has not yet been adjusted, with respect to use of an accurate detection signal from the image-taking element as it is. To this end, the information about the white balance is read from the header portion of the taken image data and processing of arithmetic operation is carried out in connection with the aforementioned processing for selectively reducing the intensity value of the B color component, so that the taken image data recorded after the adjustment of the white balance can be changed to have each intensity value in which the white balance has not yet been adjusted. By this processing, the intensity change carried out by the adjustment of the white balance is cancelled so that more accurate information of the taken image can be displayed.

Next, description will be made in the case where the correction coefficients are controlled to increase/decrease in accordance with the total lighting time of each light source LD1, LD2 of the light source device 47. Each light source LD1, LD2 shown in FIG. 1 is lit under the control of the light source control portion 51. The time for the light source control portion 51 to light each light source LD1, LD2 is counted by a timer 95. Generally, a change in intensity of light emission caused by deterioration with age is recognized in any light emitting element such as a laser diode, and the light emitting element has a characteristic in the intensity of light emission decreasing gradually with increase of the time of lighting.

Figure 12:
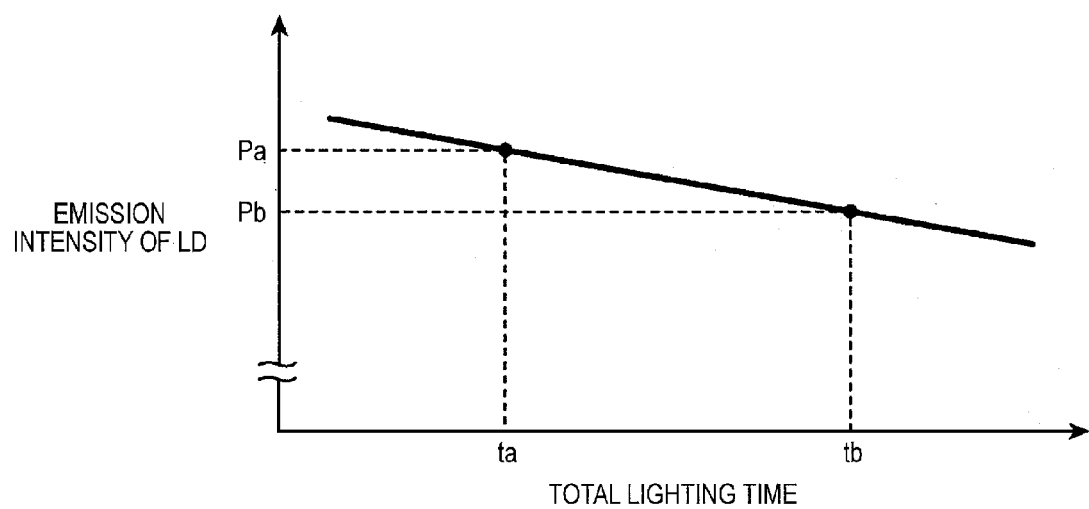
FIG. 12 is a graph showing the relationship between the total lighting time of a laser diode and the emission intensity of the laser diode.

FIG. 12 shows the relationship between the total lighting time of a laser diode and the intensity of light emission of the laser diode. Assume that the intensity of light emission is Pa when the total lighting time is ta, as shown in FIG. 12. In this case, when the correction coefficients Kb, Kg and Kr are decided for reducing the specific color component based on the intensity of light emission, the correction coefficients Kb, Kg and Kr will be displaced from their optimum values if the intensity of light emission drops down to Pb due to the total lighting time reaching tb.

Therefore, the information about the total lighting time is read from the header portion of the taken image data in order to correct each correction coefficient Kb, Kg, Kr in accordance with the light quantity from each light source for the inspection. Then, a correction value corresponding to the reduction in the intensity of light emission is obtained based on the relationship between the total lighting time and the intensity of light emission stored in the storage portion 69 (see FIG. 1), and the value of each correction coefficient Kb, Kg, Kr once set is corrected to increase/decrease by the obtained correction value. By this processing, accurate information of the taken image can be always displayed without being influenced by deterioration of each light source with age.

In the light source device 47 of the endoscopic apparatus 100 which has been described above, the narrow-band light is generated by violet laser light. However, the narrow-band light may be generated by a light emitting diode, or another configuration may be used.

Figure 13:
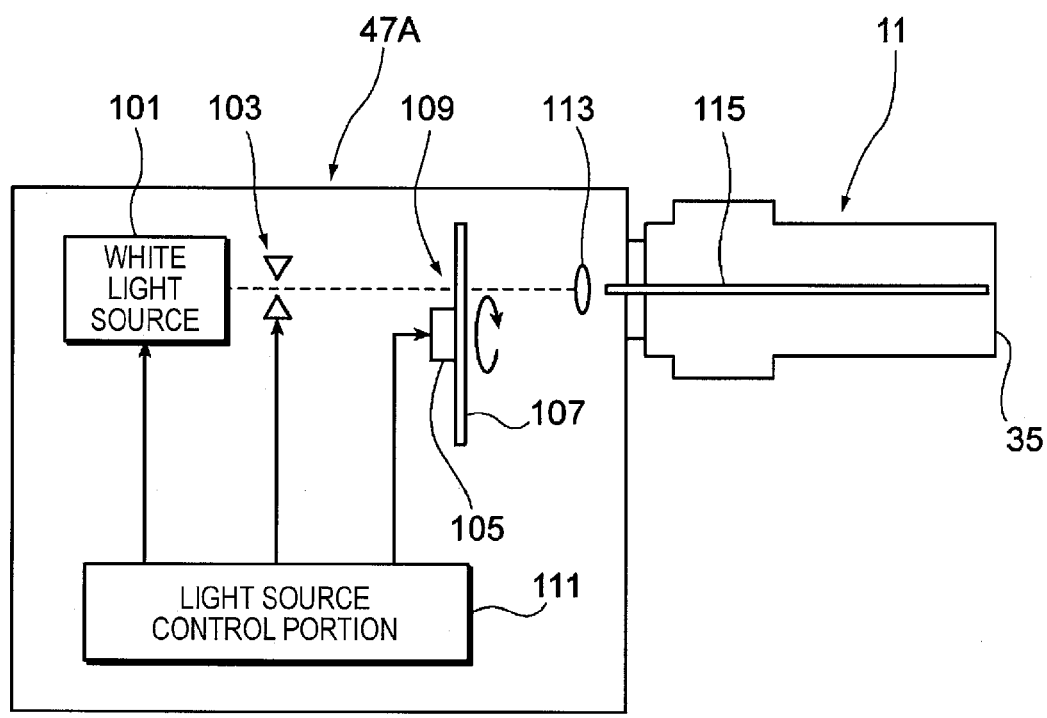
FIG. 13 is a main portion configuration diagram showing another configuration example of a light source device.

FIG. 13 shows another configuration example of the light source device. A light source device 47A has a white light source 101 such as a xenon lamp, a halogen lamp or a metal halide lamp, a movable slit 103 for adjusting the light quantity, a filter unit 109 including a motor 105 and a rotary filter 107 driven to rotate by the motor 105, and a light source control portion 111 for controlling the white light source 101, the movable slit 103 and the motor 105. An R filter, a G filter and a B filter for extracting each color light and a special light filter for extracting the aforementioned short-wavelength visible narrow-band light are disposed in the rotary filter 107.

Light transmitted through the rotary filter 107 is incident on an optical fiber bundle 115 through a condenser lens 113, passed through the optical fiber bundle 115, and guided to the front end portion 35 of the endoscope 11. Then, the light is radiated as illumination light from the endoscope front end portion 35 to the to-be-inspected body. The image-taking optics is similar to that in the configuration shown in FIG. 1, and description thereof will be therefore omitted here.

In this configuration example, an optics using a frame sequential method is formed. That is, an image is taken in sync with the rotation of the rotary filter 107 so that an R image, a G image, a B image and a narrow-band light image can be obtained sequentially. Those images (R image+G image+B image, G image+narrow-band light image, or the like) are processed to be synchronized with one another, so as to generate a color image.

In taken image data obtained when narrow-band imaging is performed using this light source device, the intensity of the B color component increases due to the narrow-band light. As described previously, therefore, processing is performed to selectively reduce the intensity of the B color component in comparison with the intensities of the other G and R color components, so that the image can be converted into an image observed in normal imaging.

The invention is not limited to the aforementioned exemplary embodiment, but the invention is also intended to be modified or applied by those skilled in the art based on the description of this specification and known techniques, and those modifications and applications are also included in the scope of protection of the invention. For example, although the intensity of the blue color component of taken image data is selectively reduced in an image obtained in narrow-band imaging, similar operation and effect to those described above can be obtained when the detected intensity of a light component radiated intensively is reduced in the case where illumination light is radiated intensively in another wavelength band than the blue color light.

As described above, the following items are disclosed in this specification.

(1) An endoscopic image display apparatus reads taken image data in which a taken image outputted from an endoscope is recorded, and reproduces and displays the taken image. The taken image data includes intensity information about a plurality of fundamental color components. The endoscopic image display apparatus includes an intensity changing unit which selectively reduces intensity of a specific color component in the taken image data by using the intensity information.

According to this endoscopic image display apparatus, even when the taken image data is data of an image taken using illumination light in which the intensity of emitted light of a specific wavelength band has been enhanced, the intensity (luminance value) of a component of the specific wavelength band is selectively reduced so that the image can be converted to have color tone in normal imaging and displayed. Thus, comparison between images or application of various image processings can be performed to improve the accuracy of endoscopic diagnosis.

(2) The endoscopic image display apparatus according to (1), the specific color component is a blue color component.

According to this endoscopic image display apparatus, the fundamental color component which is a blue color component is reduced so that, for example, an image in which a B light component has been selectively reduced from the illumination light in the narrow-band imaging can be displayed.

(3) The endoscopic image display apparatus according to (2), intensity of the blue color component includes intensity of a light component of a wavelength band of from 400 nm to 420 nm.

According to this endoscopic image display apparatus, intensity can be changed particularly for taken image data in which capillary blood vessels in a surface layer of a body tissue or microscopic patterns in a mucosal surface have been highlighted and displayed.

(4) The endoscopic image display apparatus according to any one of (1) to (3), the intensity changing unit includes an input portion which arbitrarily sets an intended value of reduction in the intensity of the specific color component.

According to this endoscopic image display apparatus, the degree of highlighted display of the specific color component can be changed, or the highlighted display can be canceled desirably.

(5) The endoscopic image display apparatus according to any one of (1) to (4), the intensity changing unit uses intensity of at least one of the fundamental color components other than the specific color component, as the intended value of reduction in the intensity of the specific color component.

According to this endoscopic image display apparatus, the intensity of the specific color component is reduced to the same level as the intensity of another fundamental color so that the color tone of the image can be made close to the color tone of an image taken in normal imaging.

(6) The endoscopic image display apparatus according to any one of (1) to (5), the taken image data is arranged to include the intensity information about the plurality of fundamental color components and information about image-taking conditions for the taken image data. The intensity changing unit includes a correction value storage portion and an intensity changing portion. The correction value storage portion stores a correction value for correcting an intended value of reduction in the intensity of the specific color component in accordance with the image-taking conditions. The intensity changing portion (i) acquires, from the correction value storage portion, the correction value corresponding to the information about the image-taking conditions read from the taken image data, (ii) corrects the intended value of reduction in the intensity with the acquired correction value, and (iii) changes the intensity of the specific color component.

According to this endoscopic image display apparatus, an intended value of reduction in the intensity of the specific color component is changed in accordance with the image-taking conditions for the taken image data so that the intensity can be changed in accordance with the image-taking conditions.

(7) The endoscopic image display apparatus according to (6), the information about the image-taking conditions is information about a to-be-observed region of a to-be-inspected body in the taken image data.

According to this endoscopic image display apparatus, the degree of reduction in the intensity of the taken image data is adjusted in accordance with each to-be-observed region of the to-be-inspected body so that the intensity can be changed properly for the to-be-observed region.

(8) The endoscopic image display apparatus according to (6), the information about the image-taking conditions is information about a white balance adjustment value for adjusting white balance of the taken image outputted by the endoscope.

According to this endoscopic image display apparatus, the degree of reduction in the intensity of the taken image data is adjusted in accordance with the adjusted value of white balance of the endoscope so that the change in intensity caused by the adjustment of the white balance can be cancelled to display more accurate information of the taken image.

(9) The endoscopic image display apparatus according to (6), the information about the image-taking conditions is lighting time information which expresses total lighting time of a light source provided in the endoscope.

According to this endoscopic image display apparatus, accurate information of the taken image can be always displayed without being influenced by deterioration of the light source with age.

(10) The endoscopic image display apparatus according to any one of (1) to (9), the taken image data is data of an image taken with illumination light whose spectroscopic profile includes laser light and light emitted from a fluorescent substance excited by the laser light.

According to this endoscopic image display apparatus, the image data is taken by irradiation with a combination of narrow-band light based on laser light and illumination light which has a broad spectroscopic profile and which is light emitted from the fluorescent substance. Accordingly, only the level of intensity of the narrow-band light component can be adjusted easily. For example, when taken image data is obtained by the image-taking element which detects a plurality of fundamental color components, the narrow-band light can be set not to be detected across a plurality of the fundamental color components but to belong to only one fundamental component different from the light emitted from the excited fluorescent substance. Thus, only the intensity of the fundamental color component the narrow-band light belongs to can be corrected easily.

What is claimed is:

1. An endoscopic apparatus comprising:
    an endoscope that takes an image using illumination light including white illumination light and light having a central wavelength of 360 to 470 nm and outputs taken image data;
    an image display apparatus that reads the taken image data output from the endoscope, and that reproduces and displays the taken image, the taken image data including intensity information about a plurality of fundamental color components in the taken image data; and
    an intensity changing unit that only reduces intensity of a blue component of the plurality of fundamental color components in the taken image data by using the intensity information,
    wherein the taken image data is arranged to include the intensity information about the plurality of fundamental color components and information about image-taking conditions for the taken image data, and
    wherein the intensity changing unit includes:
        a correction value storage portion which stores a correction value for correcting an intended value of reduction in the intensity of the blue component in accordance with the image-taking conditions; and
        an intensity changing portion which (i) acquires, from the correction value storage portion, the correction value corresponding to the information about the image-taking conditions read from the taken image data, (ii) corrects the intended value of reduction in the intensity with the acquired correction value, and (iii) changes the intensity of the blue component.

2. The endoscopic apparatus according to claim 1, wherein:

intensity of the blue component includes intensity of a light component of a wavelength band of from 400 nm to 420 nm.

3. The endoscopic apparatus according to claim 1, wherein:

the intensity changing unit includes an input portion which arbitrarily sets an intended value of reduction in the intensity of the blue component.

4. The endoscopic apparatus according to claim 1, wherein:

the intensity changing unit uses intensity of at least one of the plurality of fundamental color components other than the blue component, as an intended value of reduction in the intensity of the blue component.

5. The endoscopic apparatus according to claim 1, wherein:

the information about the image-taking conditions is information about a to-be-observed region of a to-be-inspected body in the taken image data.

6. The endoscopic apparatus according to claim 1, wherein:

the information about the image-taking conditions is information about a white balance adjustment value for adjusting white balance of the taken image outputted by the endoscope.

7. The endoscopic apparatus according to claim 1, wherein:

the information about the image-taking conditions is lighting time information which expresses total lighting time of a light source provided in the endoscope.

8. The endoscopic apparatus according to claim 1, wherein:

the taken image data is data of an image taken with illumination light whose spectroscopic profile includes laser light and light emitted from a fluorescent substance excited by the laser light.

* * * * *